United States Patent [19]

White et al.

[11] 3,989,709

[45] Nov. 2, 1976

[54] FUSED RING BENZIMIDAZOLE DERIVATIVES

[75] Inventors: Alan Chapman White, Windsor; Robin Michael Black, Porton, both of England

[73] Assignee: John Wyeth & Brother Limited, Maidenhead, England

[22] Filed: Nov. 5, 1975

[21] Appl. No.: 629,206

[30] Foreign Application Priority Data

Nov. 20, 1974 United Kingdom............. 50178/74

[52] U.S. Cl. .................. 260/294.8 B; 260/296 H; 260/297 T; 260/309.2; 424/263; 424/273
[51] Int. Cl.² ............... C07D 471/04; C07D 487/04
[58] Field of Search ......... 260/309.2, 296 H, 297 T, 260/294.8 D

[56] References Cited
OTHER PUBLICATIONS

Golubushina et al., Chem. Abst., 1972, vol. 76, No. 46158e.
Kochergin et al., Chem. Abst., 1969, vol. 70, No. 96705c.

North et al., J. Heterocycl Chem., 1969, vol. 6, pp. 655–662.

Primary Examiner—Natalie Trousof

[57] ABSTRACT

The invention relates to compounds of the formula (I)

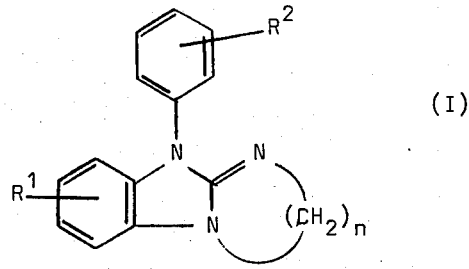

and their pharmaceutically acceptable acid addition salts. In the formula $R^1$ and $R^2$ are each hydrogen, hydroxyl, lower alkyl, lower alkoxy, trifluoromethyl or halogen. The compounds have hypotensive activity. Some also have hypoglycaemic activity.

4 Claims, No Drawings

FUSED RING BENZIMIDAZOLE DERIVATIVES

This invention relates to heterocyclic compounds. More particularly this invention relates to certain novel fused ring benzimidazole derivatives, to methods of preparing the novel derivatives and to pharmaceutical compositions containing them.

The novel compounds of the present invention are those of general formula (I)

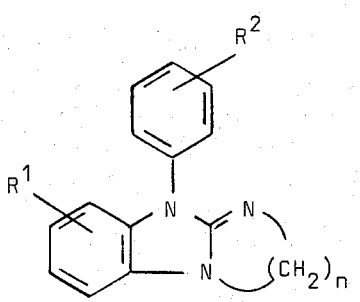

(I)

and their pharmaceutically acceptable acid addition salts. In general formula (I) $R^1$ and $R^2$ can be the same or different and each represents hydrogen, hydroxyl, lower alkyl, lower alkoxy, trifluoromethyl or halogen and $n$ represents 2 or 3.

A preferred group of compounds of the invention are those of general formula (I) above, or their pharmaceutically acceptable acid addition salts, in which $R^1$ and $R^2$ each represents hydrogen or halogen.

The term "lower" as used herein means that the radical referred to contains 1 to 6 carbon atoms. Preferably the radicals contain 1 to 4 carbon atoms.

When $n$ represents 2 the compounds are imidazo[1,2-a]-benzimidazoles of the general formula (II)

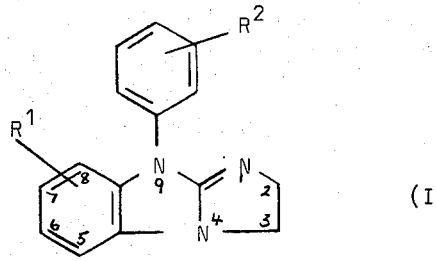

(II)

When $n$ represents 3 the compounds are pyrimido[1,2-a]benzimidazoles of the general formula (III)

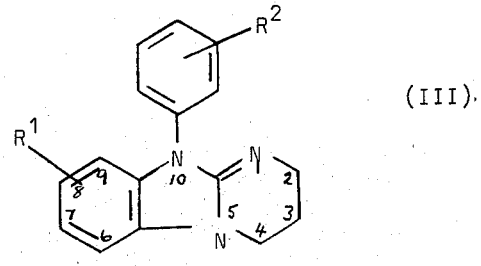

(III)

Preferably the compounds of the invention are the pyrimido[1,2-a]benzimidazoles of general formula (III) and their pharmaceutically acceptable acid addition salts.

The substituents $R^1$ and $R^2$ can be hydrogen, hydroxyl, lower alkyl (e.g. methyl, ethyl, propyl or butyl), lower alkoxy (e.g. methoxy, ethoxy, propoxy or butoxy), trifluoromethyl or halogen (e.g. chlorine, bromine). Particularly preferred compounds are those in which $R^1$ and $R^2$ are each hydrogen. Thus especially valuable compounds are 2,3,4,10-tetrahydro-10-phenylpyrimido[1,2-a]benzimidazole and its pharmaceutically acceptable acid addition salts.

The compounds of the invention may be prepared, for example, by cyclising a benzimidazole derivative of general formula (IV)

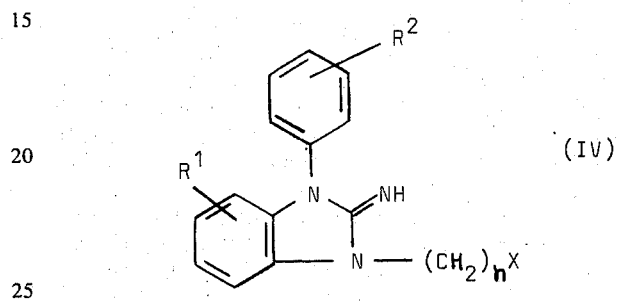

(IV)

or an acid addition salt thereof, wherein $R^1$, $R^2$ and $n$ have the meanings given above and X is a halogen atom, preferably chlorine, and if desired converting a resulting free base into an acid addition salt. The compound of general formula (IV) in its free base form or as an acid addition salt thereof may be cyclised by treatment with a base, for example an alkali metal hydroxide (e.g. sodium hydroxide) or an alkali metal alkoxide. The reaction may be carried out in an organic solvent which will dissolve the reactants and will not prevent their interaction. The reaction mixture may be heated, for example at the reflux temperature, if required.

The compounds of general formula (IV) may be prepared by treating an alcohol of general formula (V)

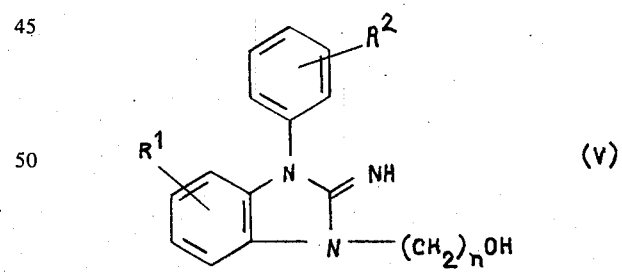

(V)

with a hydroxyl/halogen exchange reagent. By a "hydroxyl/halogen exchange reagent" is meant a reagent capable of displacing the hydroxyl group of an alcohol by a halogen atom. Typical examples are phosphorus trichloride or pentachloride and thionyl chloride. The preferred reagent is thionyl chloride. Compound (V) can be converted to compound (IV) and the latter cyclised to the compounds of the present invention without isolating compound (IV) from the reaction mixture.

Compounds of general formula (V) may be prepared by reacting an appropriately substituted 2-amino-1-phenylbenzimidazole of general formula (VI)

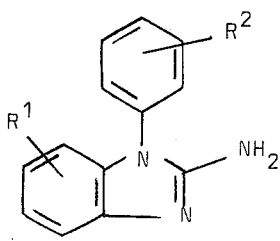

(VI)

with 2-bromoethanol or 3-bromopropanol. The bromoalcohol may, for example, be heated with the 2-amino-1-phenylbenzimidazole in an organic solvent. If the product of the reaction is the hydrobromide of the compound of general formula (V) this can be converted into the free base in the usual manner by treatment with a base. The compounds of general formula (VI) are known compounds or they can be prepared by methods known for the preparation of analogous compounds.

In an alternative method of preparing the compounds of the present invention, a compound of general formula (VI) may be reacted with a dihaloalkane of the formula (VII)

$$Y(CH_2)_nY \qquad (VII).$$

wherein $n$ is as defined above and Y is halo, preferably bromo and, if desired, converting a resulting acid addition salt to a free base. The compound of general formula (VI) may be reacted with the dihaloalkane of formula (VII) in an inert organic solvent and, if necessary, the reaction mixture may be heated, for example at the reflux temperature.

Compounds of the invention in which $n$ is 3, i.e. compounds of general formula (III) and their pharmaceutically acceptable acid addition salts, can be prepared by a further process. This further process comprises cyclising a compound of general formula (VIII)

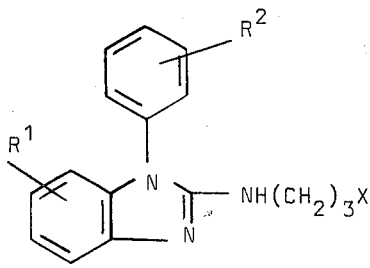

(VIII)

where $R^1$ and $R^2$ are as defined above and X is halo, preferably chloro, or an acid addition salt thereof and, if desired, converting a resulting free base into an acid addition salt. The cyclisation may be effected in a similar manner to the cyclisation of the compound of general formula (IV), for example by treatment with a base (e.g. an alkali metal hydroxide or alkali metal alkoxide) in an organic solvent. The reaction mixture may be heated (e.g. at the reflux temperature) if necessary.

The compounds of general formula (VIII) may be prepared by reacting an alcohol of general formula (IX)

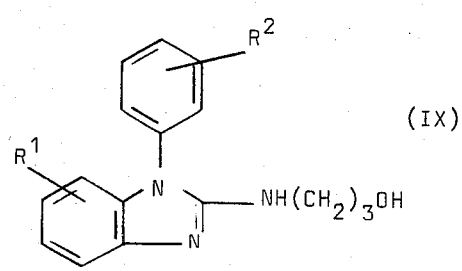

(IX)

with a hydroxyl/halogen exchange reagent (as defined above) e.g. thionyl chloride. The reaction may be carried out in an organic solvent. The compounds of general formula (IX) may be prepared by reacting the hydrochloride of a dichlorophosphorimidate of general formula (X)

(X)

with 3-aminopropan-1-ol. The reactants may be heated together. The compounds of the invention of general formula (III) may be isolated directly from the reaction mixture, thus providing another process for preparing these compounds. In general, the longer the two reactants are heated together and the higher the temperature of the reaction the greater the proportion of the compounds of general formula (III) prepared. If it is desired to prepare the compounds of general formula (IX) it is preferable to use a large excess of 3-aminopropan-1-ol and to use shorter reaction times and lower temperatures of reaction.

The dichlorophosphoroimidates of general formula (X) may be prepared from the appropriately substituted 1-phenylbenzimidazol-2-ones of general formula (XI)

(XI)

by reaction with phosphoryl chloride followed by the isolation of the compounds as their hydrochlorides. The 1-phenylbenzimidazol-2-ones of general formula (XI) are known compounds or can be prepared by methods known for analogous compounds.

In preparing the compounds of general formula (IX), the dichlorophosphorimidate of general formula (X) can be replaced by an imino chloride of general formula (XIIa) or an imino ether of general formula (XIIb)

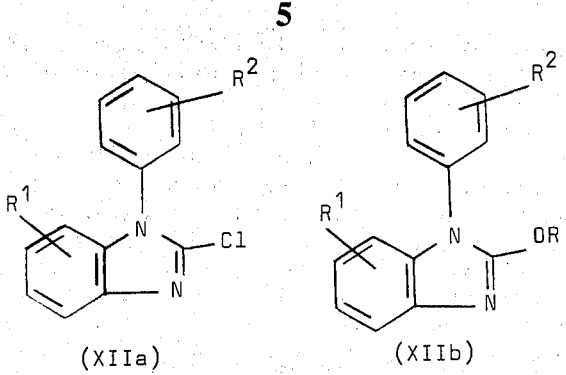

(XIIa)                (XIIb)

wherein R¹ and R² are as defined above and R is lower alkyl (e.g. ethyl). The imino chloride and the imino ether can be prepared by known processes.

If in any of the processes described above the compound of the invention is obtained as an acid addition salt, the free base can be obtained by basifying a solution of the acid addition salt. Conversely if the product is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds. Examples of suitable acids that may be used include hydrochloric, hydrobromic, tartaric, phosphoric, maleic, citric, methanesulphonic and p-toluene sulphonic acids.

The compounds of the invention show pharmacological activity. In particular, the compounds possess hypotensive activity as indicated by standard tests on warm-blooded animals. In one such procedure the compounds are administered intravenously to normotensive anaesthetised rats and the fall in diastolic blood pressure is measured. Some compounds of the invention, primarily those of formula (I) in which n is 3, also possess hypoglycaemic activity as indicated by standard pharmacological procedures. The compounds are tested for hypoglycaemic activity by administering them to fasted rats and estimating the blood sugar concentration over a five hour test period. It was found that, for example, 2,3,4,10-tetrahydro-10 -phenyl-pyrimido[1,2-a]-benzimidazole was active in this procedure when administered at a dose of 50 mg/kg.

The invention further provides a pharmaceutical composition which comprises a compound of formula (I) or a pharmaceutically acceptable acid addition salt thereof, in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "compositions" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the gylcol by weight is generally suitable. In other instances compositions can be made by dispersing the finely-divided active ingredient in aqueous starch or sodium carboxymetnyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical compositions is in unit dosage form. In such form, the compositions is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form. The daily dose of compound will vary depending upon the route of administration, the particular compound employed and the particular animal involved. The daily dose could be, for example, within the range 0.5 to 25 mg/kg depending upon the method of administration and the specific compound.

The following Examples illustrate the invention:

EXAMPLE 1

(1-phenylbenzimidazol-2-yl)phosphodichloridate

A stirred solution of 1-phenylbenzimidazolin-2-one (88 g.) in phosphoryl chloride (600 ml.) was heated under reflux for 30 mins., and then boiled for a further 5 hours with a stream of dry hydrogen chloride passing through the solution. After cooling, the excess phosphoryl chloride was removed and the crystalline residue recrystalised from boiling toluene to give the title compound as the hydrochloride, (121 g., m.p. 127°–129°C). Found: C, 42.6, H, 2.75, N, 7.55%. $C_{13}H_9Cl_2N_2O_2P$. HCl requires: C, 42.9, H, 2.75, N, 7.55%

EXAMPLE 2

2-(3-Hydroxypropylamino)-1-phenylbenzimidazole (1-Phenylbenzimidazol-2-yl) phosphodichloridate hydrochloride (18.15 g., 0.05 mole) was added portionwise to a stirred, icecooled solution of 3-aminopropan-1-ol (50ml.) and pyridine (8.1ml., 0.01 mole). The reddish mixture was then heated at 120° C for 2 hours, cooled, poured onto ice-cold water and extracted with dichloromethane. The combined extracts were washed twice with water, dried over magnesium sulphate, evaporated and the residue crystallised from ethyl acetate to give the title compound (11.15 g., m.p. 116° to 118° C).

Found: C, 71.95, H, 6.5, N, 15.6% $C_{16}H_{17}N_3O$ requires C, 71.9, H, 6.4, N, 15.7%

A hydrochloride salt (m.p. 207° to 211° C) crystallised from ethanol/ether.

Found: C, 63.25, H, 5.95, N, 13.7%. $C_{16}H_{17}N_3O.HCl$ requires: C, 63.25, H, 5.95, N, 13.8%.

EXAMPLE 3

2-(3-Chloropropylamino)-1-phenylbenzimidazole

Thionyl chloride (10 ml.) was added dropwise to a stirred solution of 2-(3-hydroxypropylamino)-1-phenylbenzimidazole (11.0 g.) in dry chloroform (100 ml.) and the solution heated under reflux for 2 hours. On dilution with ether the title compound crystallised as its hydrochloride (13.06 g., m.p. 176° to 179° C). Found: C, 59.65, H, 5.3, N, 12.95%. $C_{16}H_{16}ClN_3.HCl$ requires: C, 59.65, H, 5.3, N, 13.05%.

EXAMPLE 4

2,3,4,10-Tetrahydro-10-phenylpyrimido[1,2-a]benzimidazole 2-(3-Chloropropylamino)-1-phenylbenzimidazole hydrochloride (3.22 g., 0.01 mole) was added to a stirred solution of sodium methoxide (0.02 mole) in methanol (100 ml.) and the mixture heated under reflux for 5 hours. After removal of the methanol the residue was diluted with water, extracted with chloroform and the combined extracts washed and dried over magnesium sulphate. Evaporation of the residue gave an oil which gave the title compound as a crystalline hydrobromide salt from a solution of HBr in ethanol/ether, (2.905 g., m.p. 261°-263° C).

Found: C, 58.1, H, 5.0, N, 12.55%. $C_{16}H_{15}N_3.HBr$ requires: C, 58.2, H, 4.9, N, 12.7%.

EXAMPLE 5

2,3-Dihydro-2-imino-3-phenyl-1H-benzimidazole-1-ethanol

A solution of 2-amino-3-phenylbenzimidazole (4.18 g., 0.02 mole) and 2-bromoethanol (5.0 g., 0.04 mole) in absolute ethanol (20 ml) was heated under reflux for 24 hours. A further portion (5.0 g.) of 2-bromoethanol was added and heating continued for a further 24 hours. After removal of the solvent the residue (4.465g.)crystallised from ethanol/ether. Recrystallisation from ethanol/ether gave the pure hydrobromide of the title compound (3.545 g., m.p. 210°-212° C).

Found: C, 54.2, H, 5.0, N, 12.5%. $C_{15}H_{15}N_3O.HBr$ requires: C, 53.9, H, 4.8, N, 12.6%.

EXAMPLE 6

2,9-Dihydro-9-phenyl-3H-imidazo[1,2-a]benzimidazole a. A solution of 2,3-dihydro-2-imino-3-phenyl-1H-benzimidazole-1-ethanol [prepared by basification of the hydrobromide (2.23 g.)]and thionyl chloride (1.5 ml.) in chloroform (20 ml.) was heated under reflux for 2 hours. After removal of the solvent the oily residue was dissolved in ethanol (50 ml.), 10N aqueous sodium hydroxide solution (2ml.) added and the solution heated under reflux for 5 hours. After removal of the ethanol the residue was taken up in chloroform, washed twice with water and dried over magnesium sulphate. Removal of the chloroform gave an oil which was taken up in isopropanol and acidified with conc. hydrobromic acid. The isopropanol was evaporated and the residue crystallised from acetone. The product (0.862 g., m.p. 223°-225°C.) was recrystallised from ethanol/ether to give the title compound as its hydrobromide (0.765 g., m.p. 225°-228° C).

Found: C, 57.15, H, 4.65, N, 13.35%. $C_{15}H_{13}N_3$. HBr requires: C, 57.0, H, 4.45, N, 13.3%.

b. A solution of 2-amino-3-phenylbenzimidazole (4.18 g., 0.02 mole) and 1,2-dibromoethane (7.52 g., 0.04 mole) in toluene (40 ml.) was heated under reflux for 24 hours. After removal of the solvent the residual oil was crystallised from ethanol/ether. The product (0.950 g.) was recrystallised from ethanol/ether to give the title compound as its hydrobromide (0.875 g., m.p. 225°-228° C).

Found: C, 57.05, H, 4.5, N, 13.2%. $C_{15}H_{13}N_3.HBr$ requires: C, 57.0, H, 4.45, N, 13.3%.

EXAMPLE 7

[1-(4-Chlorophenyl)benzimidazol-2-yl)]phosphodichloridate

A stirred solution of 1-(4-chlorophenyl)benzimidazolin-2-one (40 g.) in phosphoryl chloride (300 ml.) is heated under reflux for 30 min., and then boiled for a futher 5 hours with a stream of dry hydrogen chloride passing through the solution. After cooling the excess phosphoryl chloride is removed and the residue is recrystallised to give the title compounds as the hydrochloride.

EXAMPLE 8

2-(3-Hydroxypropylamino)-1-(4-chlorophenyl)benzimidazole

[1-(4-chlorophenyl)benzimidazol-2-yl)]phosphodichloridate hydrochloride (0.03 mole) is added portionwise to a stirred, ice cold solution of 3-aminopropan-1-ol(30 ml.) in pyridine (0.06 mole). The mixture is heated to 120°-130° for 2 hours, cooled poured onto ice water and extracted with a solvent. The combined extracts are washed with water, dried over magnesium sulphate, the solvent evaporated and the residue recrystallised to give the title compound.

EXAMPLE 9

1-(4-Chlorophenyl)-2-(3-chloropropylamino)benzimidazole

Thionychloride (5ml.) is added dropwise to a stirred solution of 2-(3-hydroxypropylamino)-1-(4-chlorophenyl)-benzimidazole (5.75 g.) in chloroform (50 ml.) and the solution is heated under reflux for 2 hours. On cooling and dilution with ether the title compound is obtained as its hydrochloride.

EXAMPLE 10

2,3,4,10-Tetrahydro-10-(4-chlorophenyl)-pyrimido[1,2-a]-benzimidazole 1-(4-Chlorophenyl)-2-(3-chloropropylamino)benzimidazole (5mM) is added to a stirred solution of sodium methoxide (0.01 mole) in methanol (50 ml.) and the mixture heated under reflux for 5 hours. After removal of the methanol the residue is diluted with water, extracted with chloroform and the combined extracts washed and dried over magnesium sulphate. Evaporation gives the title compound as an oil which affords a salt on treatment with a suitable acid in an anhydrous medium.

EXAMPLE 11

2,3-Dihydro-2-imino-3-(3-chlorophenyl)-1H-5-chlorobenzimidazole-1-ethanol

A solution of 2-amino-3-(3-chlorophenyl)-5-chlorobenzimidazole (0.01 mole) [prepared from 2-amino-(3',5-dichloro)diphenylamine and cyanogen bromide] and 2-bromoethanol (0.04 moles) in absolute ethanol (20 ml.) is heated under reflux for 24 to 48 hours, until the reaction is complete. After removal of the solvent the residue is crystallised to give the title compound as the hydrobromide salt.

EXAMPLE 12

2,9-Dihydro-9-(3-chlorophenyl)-7-chloro-3H-imidazo[1,2-a]-benzimidazole

A solution of 2,3-dihydro-2-imino-3-(3-chlorophenyl)-1H-5-chlorobenzimidazole-1-ethanol [prepared from the hydrobromide (5mM)] in chloroform (20 ml.) and thionyl chloride (1.5 ml.) is heated under reflux for 2 hours. After removal of the solvent and excess thionyl chloride the oily residue is dissolved in ethanol (50 ml.) and 10N aqueous sodium hydroxide solution (2ml.) added. The solution is then heated under reflux until the reaction is complete. After removal of the ethanol the residue is dissolved in chloroform and washed with water. After drying over magnesium sulphate the solvent is removed under reduced pressure and the residual oil is converted to an acid addition salt of the title compound in the usual way.

We claim:

1. A compound selected from the group consisting of bases having the formula (I)

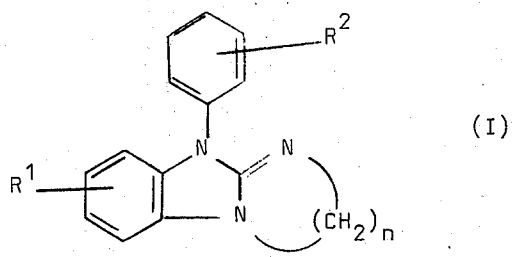

and the pharmaceutically acceptable acid addition salts thereof, wherein $R^1$ and $R^2$ each represent hydrogen, hydroxyl, lower alkyl, lower alkoxy, trifluoromethyl or halogen and $n$ represents 2 or 3.

2. A compound according to claim 1 wherein $R^1$ and $R^2$ each represent hydrogen or halogen.

3. A compound according to claim 1 which is 2,3,4,10-tetrahydro-10-phenylpyrimido[1,2-a]benzimidazole or a pharmaceutically acceptable salt thereof.

4. A compound according to claim 1 which is 2,9-dihydro-9-phenyl-3H-imidazo[1,2-a]benzimidazole or a pharmaceutically acceptable salt thereof.

* * * * *